United States Patent [19]

Alvarado

[11] Patent Number: 5,554,124
[45] Date of Patent: Sep. 10, 1996

[54] UNIVERSAL GASKET FOR LAPAROSCOPIC CANNULA

[76] Inventor: Alfredo Alvarado, 4310 Bayview Dr., Ft. Lauderdale, Fla. 33308

[21] Appl. No.: 235,873

[22] Filed: May 2, 1994

Related U.S. Application Data

[63] Continuation-in-part of Ser. No. 27,718, Mar. 8, 1993, abandoned.

[51] Int. Cl.$^6$ .................................................. A61M 39/06
[52] U.S. Cl. ........................ 604/167; 604/169; 604/248; 277/212 FB; 251/344
[58] Field of Search ........................... 606/185; 604/167, 604/169, 236, 237, 248, 256, 32; 277/212 FB; 251/344, 345

[56] References Cited

U.S. PATENT DOCUMENTS

| | | | |
|---|---|---|---|
| 4,177,814 | 12/1979 | Knepshield et al. | 604/167 X |
| 5,127,626 | 7/1992 | Hilal et al. | 604/256 X |
| 5,158,553 | 10/1992 | Berry et al. | 604/248 |
| 5,256,150 | 10/1993 | Quiachon et al. | 604/169 X |
| 5,350,364 | 9/1994 | Stephens et al. | 604/167 |

*Primary Examiner*—Michael H. Thaler
*Attorney, Agent, or Firm*—Oltman and Flynn

[57] ABSTRACT

A laparoscopic cannula gasket apparatus for sealing around an instrument within a cannula includes a first member having an internal passageway, an elastic sleeve member within the passageway, a structure for securing a first segment of the sleeve member to the passageway, a second member rotatably connected to the first member, a structure for securing a second segment of the sleeve member to the second member, the first and second segments of the sleeve member being spaced apart so that a portion of the sleeve member extends between the first and second segments, such that rotating the second member relative to the first member stretches the portion of the sleeve member between the first and second segments to progressively form an annular diaphragm extending radially inward from the passageway to make sealing contact with the instrument. The first member is preferably a cylinder attached to an end of a cannula by a flattened out end portion so that the passageway is essentially coaxial and aligned with the longitudinal axis of the cannula. The elastic sleeve member is preferably a latex material. The structure for securing the first segment of the sleeve member preferably includes a recess in the passageway and an annular member fit within the recess, between which the first segment is compressed. The structure for securing the second segment preferably includes a port in the second member having a port edge and an annular member fit against the port edge, between which the second segment is compressed.

9 Claims, 2 Drawing Sheets

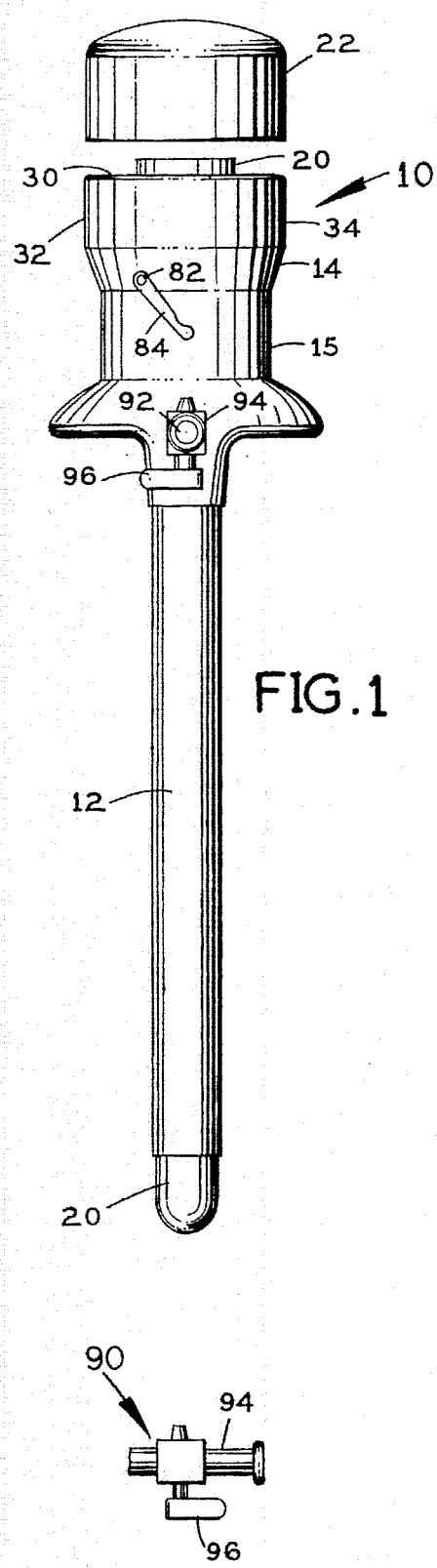
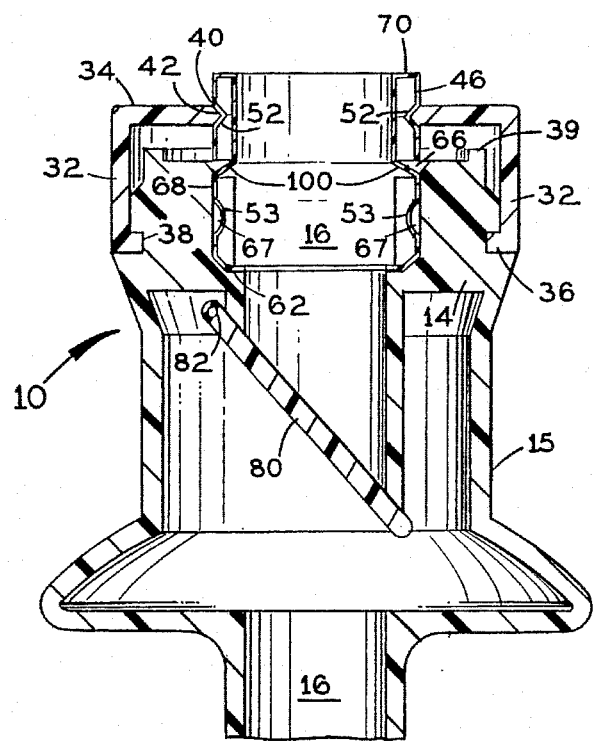
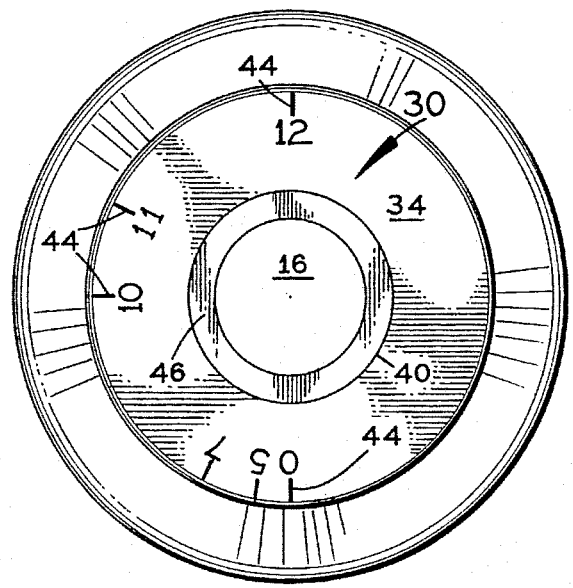
FIG. 1
FIG. 1a
FIG. 2
FIG. 3

UNIVERSAL GASKET FOR LAPAROSCOPIC CANNULA

This application is a continuation-in-part of application Ser. No. 08/027,718, filed on Mar. 8, 1993 now abandoned.

BACKGROUND OF THE INVENTION

1. Field of the Invention

The present invention relates generally to the field of cannulas for laparoscopic examination and surgery, and more specifically to a gasket assembly for sealing around an instrument to prevent loss of air under pressure inside the abdominal cavity, the assembly including a first member with a central internal passageway for receiving instruments, the passageway containing a universal gasket including a cap having a central port and a lip with an inward projecting flange rotatably fit into a groove around the circumference of the first member, the cap having a central hole aligned with the passageway and a first ring with a circumferential exterior groove fit resiliently over the edge of a the central port, a second ring being resiliently fitted into a recess around the passageway entrance, and a latex sleeve fit at one end snugly between the first ring and the cap and at the other end snugly between the second ring and the first member, so that rotating the cap and first ring relative to the second ring stretches the middle portion of the sleeve extending between the rings, the tension in the sleeve in turn causing the middle portion to close radially inward and to make sealing contact with an object extending through the passageway, regardless of the diameter of the object, and rotating the cap in the opposite direction releases the object and opens the passageway.

2. Description of the Prior Art

There have long been cannulas for providing laparoscopic access for various procedures. Some of these cannulas have required the use of various reducers to close the space between the cannula walls and each instrument placed within the cannula, to prevent loss of gas from the abdominal cavity. A problem with these reducers is that a different reducer must be used for each instrument having a diameter different from that of the previous instrument. Changing reducers can lead to loss of critical time and carries the risk that the proper reducer may be missing at a crucial moment.

Berry, et al., U.S. Pat. No. 5,158,553, issued on Oct. 27, 1992, discloses a rotatably actuated constricting catheter valve. Berry includes a hub which is joined to the catheter, and a rotatable cap which is joined to the hub. An elastomeric sleeve is positioned in an opening through the interior of the valve body. One end of the elastomeric sleeve is joined to the rotatable cap and the other end is joined to the hub, so that turning the cap collapses the sleeve around an instrument within the opening. The Berry sleeve must extend through two annular members, necessarily making the collapsing sleeve portion relatively long. A problem with Berry is that when the Berry members are rotated to close the valve, the elongated sleeve collapses to form essentially a tubular contact surface, gripping the instrument along a wide band. This wide sleeve contact creates a high friction grip which prevents ready axial or rotational movement of the instrument within the opening or passageway. While such movement may not be necessary to the catheter use emphasized in Berry, it is necessary in laparoscopic surgery.

Knepshield, et al., U.S. Pat. No. 4,177,814, issued on Dec. 11, 1979, reveals a self-sealing cannula. Knepshield includes a slotted elastomeric valve positioned in a valve seat with the slot disposed over the passage. The elastomeric valve is compressed to seal the slot, thus sealing the cannula passage around any instrument within the passage. Knepshield includes a thick block or mass of elastic material which has a closed central slit and is compressed in a contracting compartment to create a sealing bulge around an instrument. The problems of Berry et al. are again presented.

It is thus an object of the present invention to provide a universal gasket assembly which can seal around an infinite variety of instrument diameters and thus replaces reducers.

It is another object of the present invention to provide such a gasket assembly which can be readily and securely incorporated into existing laparoscopic cannulas.

It is another object of the present invention to provide such a gasket assembly which uses a short sleeve portion to generate a thin diaphragm gasket, making essentially line contact with an instrument in the assembly, so that instruments can be moved within the assembly with minimal friction resistance It is still another object of the present invention to provide such a gasket assembly which can simplify and expedite the performance of many laparoscopic procedures.

It is still another object of the present invention to provide a method to make an air-tight connection between the gasket and the cannula.

It is finally an object of the present invention to provide such a gasket assembly which can be inexpensively manufactured from well known, conventional surgical materials.

SUMMARY OF THE INVENTION

The present invention accomplishes the above-stated objectives, as well as others, as may be determined by a fair reading and interpretation of the entire specification.

A laparoscopic cannula gasket apparatus is provided for sealing around an instrument within a cannula, including a first member having an internal passageway, an elastic sleeve member within the passageway, the elastic sleeve member being formed of a sleeve member material having an average thickness, structure for securing a first segment of the sleeve member to the passageway, a second member rotatably connected to the first member, structure means for securing a second segment of the sleeve member to the second member, the first and second segments of the sleeve member being spaced apart so that a gasket-forming portion of the sleeve member extends between the first and second segments, so that rotating the second member relative to the first member stretches the portion of the sleeve member between the first and second segments to progressively form an annular diaphragm of stretched sleeve member material extending radially inwardly from the passageway to progressively close around and make sealing contact with the instrument, where the structure for securing the second segment of the sleeve member includes a port in the second member having a port edge and a second annular brace having an axial depth and having two member edges and fit within the port and against the port edge, the sleeve member second segment being anchored between the port edge and the second annular brace, and extending over a member edge of the second annular brace opposite the first member, and then doubling back inside and through the second annular brace, where the passageway in the first member has an inner wall, and the structure for securing the first segment of the sleeve member includes a first annular brace having an axial depth and which is positioned within and across the passageway to follow the passageway inner wall, and the first annular brace is spaced apart from the second annular brace a distance greater than the average thickness of the sleeve member material for permitting the sleeve member to pass between the first and second annular braces without binding between the first and second annular braces when one the annular brace is rotated relative to the other annular brace, and the sleeve member extends between the first annular brace and the passageway inner wall so that the first segment is anchored between the first annular brace and the passageway inner wall, so that the length of the gasket-forming portion of the sleeve member exposed within the passageway is limited to substantially the axial depth of the second annular brace, to form a thin diaphragm gasket to permit minimally restricted movement of laparoscopic instruments within the internal passageway while the instruments are engaged by the gasket.

The first member is preferably a cylinder attached to an end of a cannula by a flattened out segment so that the passageway is essentially coaxial and aligned with the longitudinal axis of the cannula. The elastic sleeve member is preferably formed of a latex material. The structure for securing the first segment of the sleeve member preferably includes a recess in the passageway and a first annular member fit within the recess, between which the first segment is compressed. This connection is made air-tight by means of epoxy or similar cement that is accumulated in a small space around the first segment of the sleeve. The structure for securing the second segment of the sleeve member preferably includes a port in the second member having a port edge and an annular member fit against the port edge, between which the second segment is compressed. The apparatus preferably additionally includes a flap valve within the passageway, the flap valve being mounted on a pin member and biased into a closed position with a biasing mechanism. An end of the pin member preferably protrudes through the exterior of the first member, and additionally includes a lever attached to the protruding end of the pin member. The second member is preferably a cap having a lip and an inwardly directed flange on the lip slidably fitting into a circumferential groove around the exterior of the first member. The cap optionally includes calibration markings for indicating how far the cap is rotated relative to the first member. The apparatus may additionally include a nozzle protruding from the first member to introduce gas into the passageway, from an end of a hose. The nozzle additionally includes a stopcock for controlling the flow of gas through the nozzle.

A laparoscopic cannula gasket apparatus is also provided for sealing around an instrument within a cannula, including a first member having a first opening with a first opening inner surface, an elastic sleeve member within the first opening, the elastic sleeve member being formed of a sleeve member material having an average thickness, structure for securing a first segment of the sleeve member to the first opening inner surface, a second member having a second opening with a second opening inner surface and being rotatably connected to the first member, structure for securing a second segment of the sleeve member to the second member, the first and second segments of the sleeve member being spaced apart so that a gasket-forming portion of the sleeve member extends between the first and second segments, so that rotating the second member relative to the first member stretches the portion of the sleeve member between the first and second segments to progressively form an annular diaphragm of stretched sleeve member material extending radially inwardly from the opening inner surfaces to progressively close around and make sealing contact with the instrument, where the structure for securing the first segment of the sleeve member includes a first annular brace having an axial depth and having two member edges and positioned within and across the first opening to follow the first opening inner surface, where the structure for securing the second segment of the sleeve member includes the second member second opening and a second annular brace having an axial depth and fit within the second opening and against the second opening inner surface, and the sleeve member extends between the second annular brace and the first opening inner surface so that thesecond segment is anchored between the second annular brace and the second opening inner surface, so that the length of the gasket-forming portion of the sleeve member exposed within the first and second members is limited to substantially the axial depth of the first annular brace, to form a thin diaphragm gasket to permit minimally restricted movement of laparoscopic instruments within the first and second members while the instruments are engaged by the gasket, where the first annular brace is spaced apart from the second annular brace a distance greater than the average thickness of the sleeve material for permitting the sleeve member to pass between the first and second annular braces without binding between the first and second annular braces when one the annular brace is rotated relative to the other annular brace, the sleeve member second segment being anchored between the first opening inner surface and the first annular brace, and extending over a member edge of the first annular brace opposite the second member, and then doubling back inside and through the first annular brace.

BRIEF DESCRIPTION OF THE DRAWINGS

Various other objects, advantages, and features of the invention will become apparent to those skilled in the art from the following discussion taken in conjunction with the following drawings, in which:

FIG. 1 is a side view of the inventive gasket assembly shown mounted on a cannula with a trocar inserted through the gasket, the flap valve and the cannula. FIG. 1a is a close-up projection view of the nozzle assembly seen in FIG. 1.

FIG. 2 is a cross-sectional side view of the preferred embodiment of the inventive gasket assembly, having the optional flap valve feature.

FIG. 3 is a top view of the cap of the gasket assembly showing the calibration markings and having the universal gasket open.

DETAILED DESCRIPTION OF THE PREFERRED EMBODIMENTS

Figure 4:
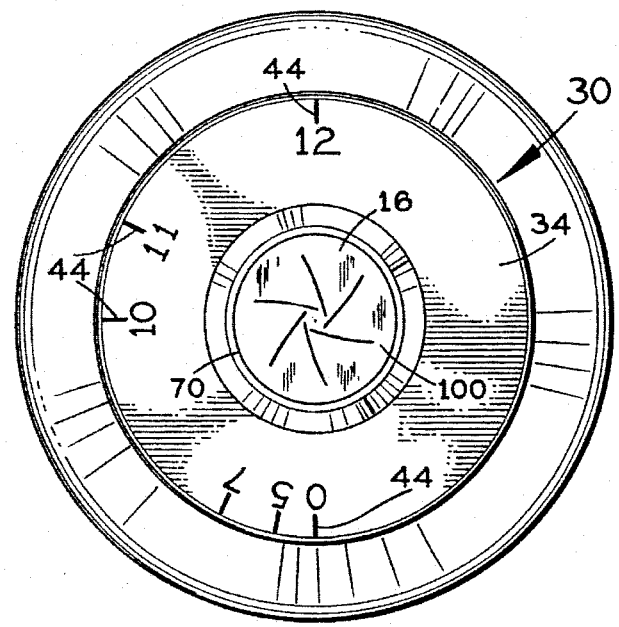
FIG. 4 is a view as in FIG. 3, except that the universal gasket is shown closed.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIGS. 1–3, a universal gasket assembly 10 is disclosed for use with a laparoscopic cannula 12 for inserting through a patient's abdominal wall. Gasket assembly 10 includes a first member 13 with an internal passageway 16 for receiving trocar or laparoscopic instruments 20. First member 13 comprises a cylindrical portion to engage the flange of a cap 34 and a flattened-out portion 15 to accommodate a flap valve 80 and a nozzle 90.

Gasket assembly 10 includes an inventive universal gasket 30 for sealing passageway 16 around an instrument 20 of any diameter to prevent escape of gas from the abdominal cavity. Universal gasket 30 includes a cap 34 having a lip 32 with an inward projecting flange 36 rotatably fit into a groove 38 around the cylindrical portion 14 of member 13. At the cylindrical portion 14 of member 13 there is a lip 39 that prevents spillage of fresh cement between lip 32 of cap 34 and first member 13. Cap 34 has a central port 40 with an edge 42, and has calibration markings 44 around the cap 34 perimeter. A first ring 46 has a circumferential external groove 52 which fits resiliently over edge 42. A second ring 62 has a circumferential external groove 53 and is resiliently fit into a recess 66 extending around the entrance 68 of passageway 16. An elastic sleeve 70 is fit at one end snugly between first ring 46 and edge 42 of port 40, then turns around the outer edge of ring 46 to become positioned inside ring 46. Sleeve 70 is fit at its other end between second ring 62 and recess 66 of cylindrical portion of member 13. It should be noted that there is a small space at groove 53 between the sleeve and recess 66 intended to accumulate an epoxy or similar cement in order to make the connection between sleeve 70 and first member 13 airtight.

Passageway 16 contains a flap valve 80 mounted on a pin 82 and biased toward a closed position with a spring, for preventing the escape of gas from the abdomen. Flap valve 80 is deflected into an open position when a trocar or an instrument 20 is inserted through passageway 16 and cannula 12. Flap valve 80 also may be operated with an external lever 84 attached to pin 82.

A nozzle assembly 90 is optionally provided, including an opening 92 in the flat portion of member 14 to insufflate gases through passageway 16. A nozzle member 94 protrudes from opening 92, and a stopcock valve 96 is provided in nozzle 94. See FIGS. 1 and 1a.

Sleeve 70 is preferably made of a latex material. The remainder of gasket assembly 10 is preferably made of a suitable plastic.

Method

Figure 5:
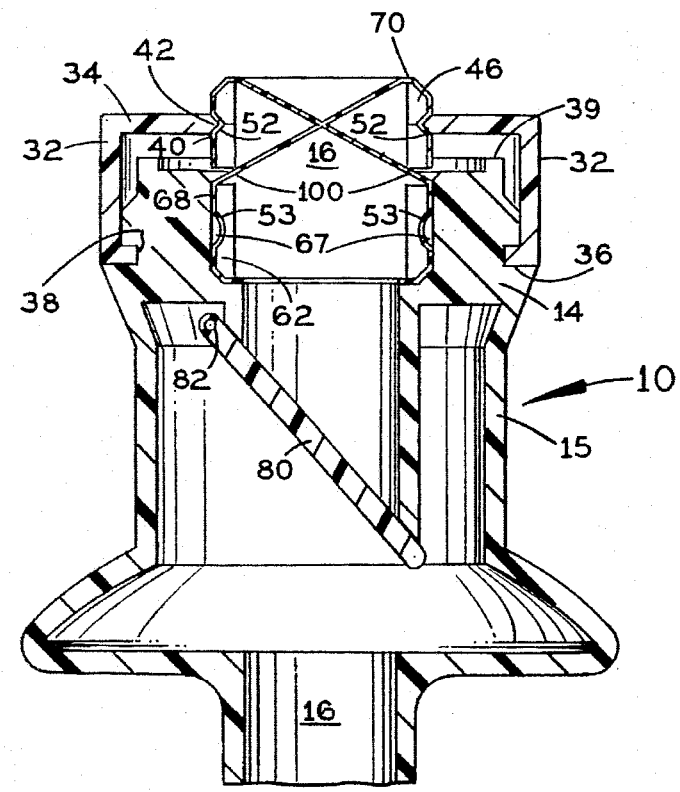
FIG. 5 is a cross-sectional side view of the assembly with the gasket closed as in FIG. 4, showing the short axial depth of the sleeve, and the sharp converging contact edge of the sleeve, which would make essentially line contact with an instrument.

In practicing the invention, the following method may be used. Rotating cap 34 and first ring 46 relative to second ring 62 in a given direction stretches the middle portion 100 of sleeve 70 between rings 46 and 62. The tension in the latex in turn causes middle portion 100 to progressively close radially inward and make sealing contact with an instrument 20 extending through passageway 16. Middle portion 100 stretches to form a diaphragm similar to the shutter of a camera. See FIGS. 4 and 5. Sealing contact with an instrument 20 is created regardless of the diameter of instrument 20. This contact is very narrow, and is effectively line contact with instrument 20, creating an air-tight seal and yet permitting the instrument 20 to be freely moved and manipulated within passageway 16. Rotating cap 34 in the opposite direction releases instrument 20 and opens passageway 16.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A laparoscopic cannula gasket apparatus for sealing around an instrument within a cannula, comprising:

a first member having an internal passageway, an elastic sleeve member within said passageway, said elastic sleeve member being formed of a sleeve member material having an average thickness, means for securing a first segment of said sleeve member to said passageway, a second member rotatably connected to said first member, means for securing a second segment of said sleeve member to said second member, said first and second segments of said sleeve member being spaced apart so that a gasket-forming portion of said sleeve member extends between said first and second segments, such that rotating said second member relative to said first member stretches said portion of said sleeve member between said first and second segments to progressively form an annular diaphragm of stretched sleeve member material extending radially inwardly from said passageway to progressively close around and make sealing contact with said instrument, wherein said means for securing said second segment of said sleeve member comprises a port in said second member having a port edge and a second annular brace having an axial depth and having two member edges and fit within said port and against said port edge, said sleeve member second segment being anchored between said port edge and said second annular brace, and extending over a member edge of said second annular brace opposite said first member, and then doubling back inside and through said second annular brace, wherein said passageway in said first member has an inner wall, and said means for securing said first segment of said sleeve member comprises a first annular brace having an axial depth and which is positioned within and across said passageway to follow said passageway inner wall, and said first annular brace is spaced apart from said second annular brace a distance greater than said average thickness of said sleeve member material for permitting said sleeve member to pass between said first and second annular braces without binding between said first and second annular braces when one said annular brace is rotated relative to the other said annular brace, and said sleeve member extends between said first annular brace and said passageway inner wall such that said first segment is anchored between said first annular brace and said passageway inner wall, such that the length of said gasket-forming portion of said sleeve member exposed within said passageway is limited to substantially the axial depth of said second annular brace, to form a thin diaphragm gasket to permit minimally restricted movement of laparoscopic instruments within said internal passageway while said instruments are engaged by said gasket.

2. An apparatus according to claim 1, wherein said first member is essentially a cylinder attached to an end of a cannula such that said passageway is essentially coaxial and substantially aligned with the longitudinal axis of said cannula.

3. An apparatus according to claim 1, wherein said elastic sleeve member is formed of latex material.

4. An apparatus according to claim 1, wherein said means for securing said first segment of said sleeve member comprises a recess in said passageway and said first annular brace fits within said recess, between which said first segment is compressed.

5. An apparatus according to claim 4, further including a pin member wherein an end of said pin member protrudes through the exterior of said first member, additionally comprising a lever attached to said end of said pin member.

6. An apparatus according to claim 1, wherein said second member is a cap having a lip and an inwardly directed flange on said lip slidably fitting into a circumferential groove around the exterior of said first member.

7. An apparatus according to claim 6, wherein said cap includes calibration markings for indicating how far said cap is rotated relative to said first member.

8. An apparatus according to claim 1, additionally comprising a nozzle protruding from said first member in gas communication with said passageway, for receiving an end of a hose.

9. An apparatus according to claim 8, wherein said nozzle additionally comprises a nozzle valve for controlling the flow of gas through said nozzle.

* * * * *